Figure 1:
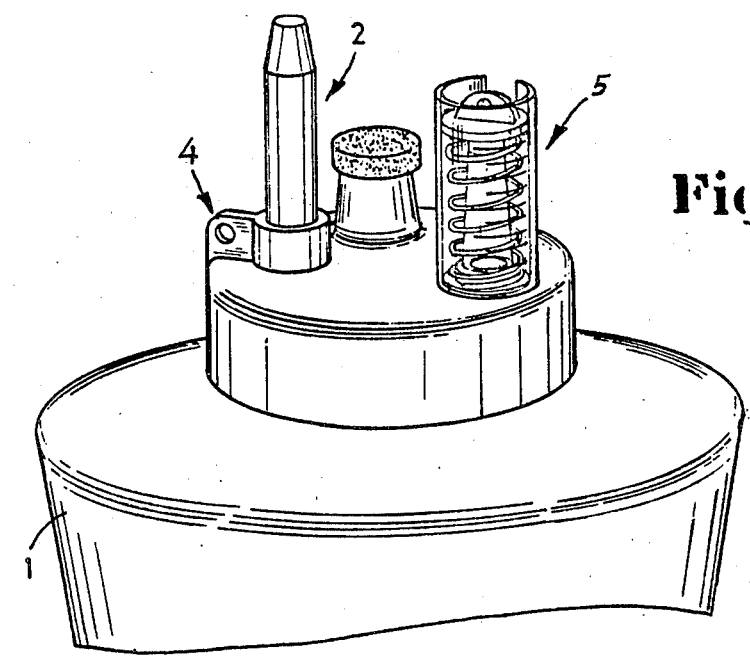

United States Patent [19]

Harle

[11] 4,373,528
[45] Feb. 15, 1983

[54] SUCTION BOTTLE FOR SUCKING OUT SECRETIONS FROM WOUND CAVITIES

[76] Inventor: Anton Harle, Munster-Roxel, Fed. Rep. of Germany

[21] Appl. No.: 245,011

[22] Filed: Mar. 18, 1981

[30] Foreign Application Priority Data

Mar. 22, 1980 [DE] Fed. Rep. of Germany ....... 3011163

[51] Int. Cl.³ .............................................. A61M 1/00
[52] U.S. Cl. .................................. 128/276; 116/272; 116/276; 73/744
[58] Field of Search ............... 128/276, 277, 278, 760, 128/761, 771; 116/272, 276; 137/557; 73/744, 146.8

[56] References Cited

U.S. PATENT DOCUMENTS

| 1,565,423 | 12/1925 | Dailey | 73/744 |
| 2,292,474 | 8/1942 | Paxton | 73/744 |
| 4,023,416 | 5/1977 | Ormsby | 73/744 |
| 4,222,276 | 9/1980 | De Rogatis | 73/744 |

FOREIGN PATENT DOCUMENTS

| 7336232 | 10/1973 | Fed. Rep. of Germany. |
| 7902325 | 7/1979 | Fed. Rep. of Germany. |
| 2246280 | 5/1975 | France ................. 128/276 |
| 2041756 | 9/1980 | United Kingdom. |

Primary Examiner—Richard J. Apley
Assistant Examiner—J. L. Kruter
Attorney, Agent, or Firm—Merchant, Gould, Smith, Edell, Welter & Schmidt

[57] ABSTRACT

A suction bottle for evacuating secretions from wounds is disclosed. The bottle includes a vacuum indicator arrangement located over a pressure opening 6 in the bottle, a sealing tube 7, a return spring 9, and a graduated scale bearer 10. In response to changes in pressure within the bottle, abutment 8 is caused to travel within graduated scale bearer 10, thus indicating the pressure within the bottle.

4 Claims, 5 Drawing Figures

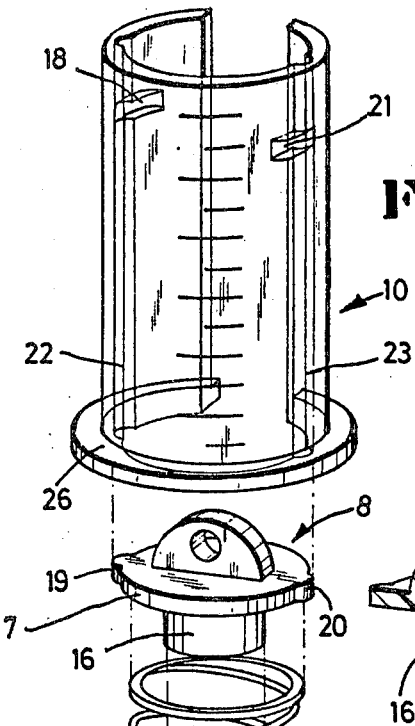
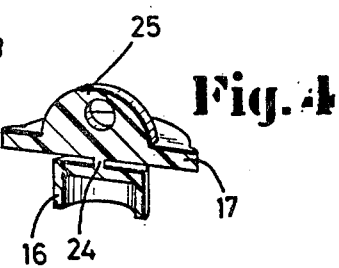
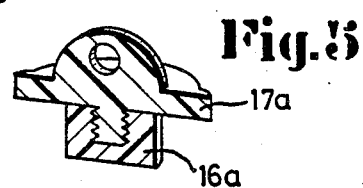
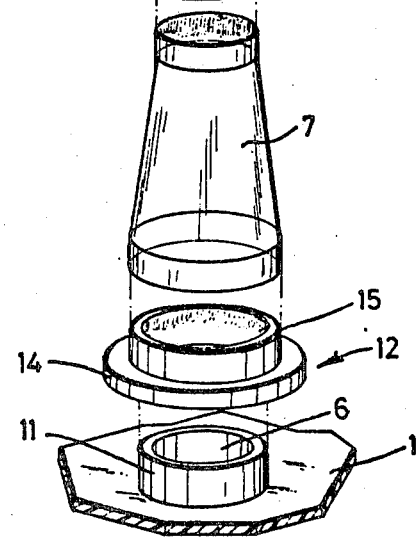

SUCTION BOTTLE FOR SUCKING OUT SECRETIONS FROM WOUND CAVITIES

The invention relates to a suction bottle for sucking out secretions from wound cavities, with an arrangement for checking the vacuum sealing off a pressure opening in the suction bottle, and with a connecting stub for a suction line.

Description in DE-GM (German Utility Model) No. 73 36 232 is a plastic suction bottle that serves for sucking out secretions from wound cavities, with the suction bottle displaying a connecting part for attaching the actual suction line, and is combined with a pressure indicator. In the case of the known arrangement, the pressure indicator is structured as a bellows and is supposed to indicate to the doctor or nursing personnel, by means of its corresponding expansion, the vacuum that is present in the suction bottole. In practice, it has turned out that the use of bellows as a pressure indicating arrangement is inexact, wherewith, in particular in the case of lengthy storage, there occurs a fatiguing of the material that leads to inaccuracies of the indication and, therewith, to false conclusions on the part of the doctor or of the nursing personnel.

A suction bottle for wound drainage is also described in DE-GM No. 79 02 325, where the suction bottle is equipped with a pressure indicator structured as a bellows, but additionally displaying a scale bearer that is combined with the indicating arrangement, whereby the pressure indication is supposed to be rendered capable of being estimated with more certainty.

The task set forth for the invention is to improve the indication of pressure in these types of precedingly described suction bottles such that the pressure indicator is exact and, in this fashion, provides a positive indication of the level of pressure prevailing in the suction bottle.

This task set forth for the invention is resolved by means of a return spring for the vacuum indicator arrangement, produced from a springy-elastic material, that is supported on the outside of a sealing tube enclosing the pressure opening between the top end of the suction bottle and an abutment fixed to the sealing tube, which is fixed on the one end, in sealing fashion, to the suction bottle and closed off on the other end. The return spring made of a springy-elastic material is preferentially of steel since these types of steel springs display an excellent spring constant and are, at the same time, obtainable at a good price.

Previously, the use of metal components in conjunction with suction bottles was avoided by the technical world since, in the case of such metal components, there had to be assurance that these latter would not get into the poisonous waste product removal system, which usually consists of combustion furnaces. The insertion of a metal return spring, for example to substitute for the bellows, caused difficulties since it must further be assured that, for example when removing the metal spring before discarding the filled suction bottle, it must be assured that the suction bottle openings are closed so that an outflow of germ-containing wound secretion was excluded. The inventor therefore had to solve the problem, on the one hand, of obtaining a return mechanism displaying a very high spring constant and thereby making the indicator arrangement work in a positive fashion, on the other hand care had to be taken that this return spring can be removed and that, nevertheless, the suction bottle remains hermetically sealed.

All of these problems are resolved in particularly advantageous fashion by means of the further mentioned measures in the claims and, indeed, advantageous on the one hand for the nursing personnel handling the suction bottle, advantageous on the other hand for the production shops making the suction bottles, so that it is possible to place at the disposal of the nursing personnel a suction bottle produced in a cost-favorable fashion.

Starting out from the basic consideration in accordance with the present invention, that the return spring must be arranged on the outside of a tube sealing off the pressure opening of the suction bottle, it is further proposed that the element supporting the return spring against the bottle, the so-called abutment, be replaceable so that, therewith, a detachment of this abutment from the sealing tube is assured. Achieved in this fashion is that replacement of the spring is possible, for example for obtaining different spring constants, so that it becomes possible to deliver suction bottles with different pressures, with the indicator arrangement capable of being adapted to the output pressure prevailing in the bottle. It is self-understood that in doing this, it is possible to proceed such that two or more return springs can be combined in place of a single return spring, so that different springy ranges, e.g. first a fine measurement range and then a rougher measurement range, can be obtained on the indicator arrangement.

Examples of embodiment of the invention will be explained in the following with the aid of the drawing. Here the drawing shows in FIG. 1 pictorially, the view onto a top portion of a suction bottle in accordance with the invention, in FIG. 2 a view in accordance with FIG. 1, where the pressure indicator arrangement is partially cut through, in FIG. 3 in an exploded illustration, the components of the actual pressure indicator arrangement, in FIG. 4 in a cut view illustration, a first form of embodiment of the abutment, and in FIG. 5 in a cut view illustration, a second form of embodiment of the abutment.

Figure 2:
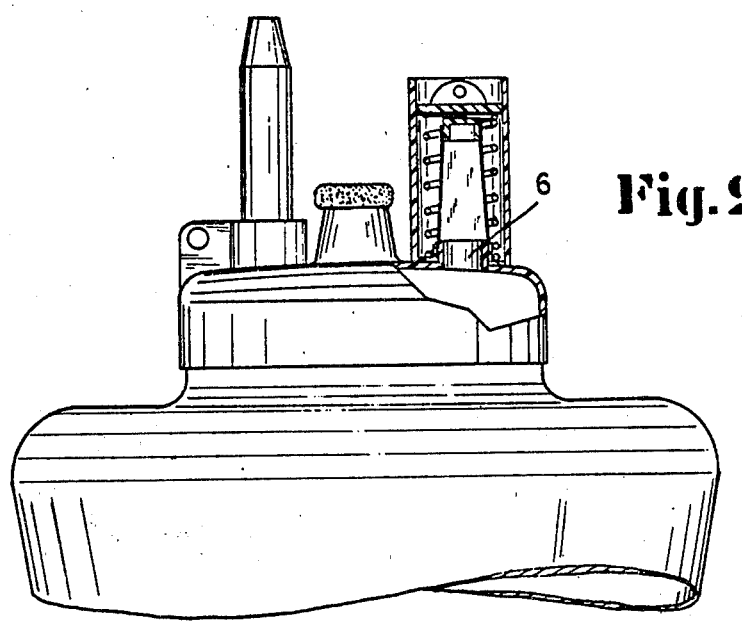

Designated with 1 in FIG. 1 is the actual suction bottle that displays at its top end a connecting stub 2 for the suction line. Illustrated at 3 is a prick-through cap that enables checking, by puncturing with a checking cannula, the inside of the suction bottle and the sterile conditions, while maintaining the vacuum. The suspension eyelet serving for supporting the suction bottle is illustrated at 4. This type of suction bottle is state of the art.

Combined with the suction bottle, at the top end of the suction bottle, there is also a vacuum indicator arrangement 5 which, however, self-understood, can also be arranged at another point of the suction bottle.

The vacuum indicator arrangement consists essentially of the pressure opening 6 provided in the suction bottle itself, a sealing tube 7, an abutment 8, along with a return spring 9 and—only in the case of the example of embodiment illustrated—a scale bearer 10, with these components capable of being recognized more clearly from the illustration in FIG. 3.

In the example of embodiment illustrated, the pressure opening 6 is structured in fashion of a connecting stub, i.e. provided at the top end of the actual suction bottle 1 is an annular stub 11. Capable of being placed over this annular stub 11 is an L-shaped attachment ring 12 which, by means of its horizontal ring area 14, can be cemented to the top end of the suction bottle 1, while the vertical ring area 15 supports, on its outer side, in sealing fashion, the sealing tube 7, while the inner side of this ring area 15 is fixed, in sealing fashion, to the stub 11.

The sealing tube 7 can consist of simple foil that is secured against collapsing by means of stabilizing rings or the like, and displays a length that is greater than the spring (travel) path, and merely has the task of sealing the pressure opening 6 and, therewith, the pressure prevailing in the interior of the bottle against ambient pressure. Resulting from this, on the one hand, is a pressure-tight fixation to the ring area 15, on the other hand a tight fixation of the top end of the sealing tube 7 to a somewhat conically embodied closure stopper part 16 of the abutment 8. Connecting to the top closure stopper 16 of abutment 8 is the actual support area 17 of abutment 8, with the return spring resting against this support area 17, being supported at the bottom on the top side of the horizontal ring area 14.

In this fashion, the return spring normally, i.e. when there is no vacuum present in the bottle 1, holds the abutment 8 in its upper position.

If a vacuum does prevail in the bottle 1, then this vacuum strives to draw the abutment 8 downwardly toward the pressure opening 6 and, indeed, against the action of the return spring 9.

The scale bearer 10 displays on its outer side a graduated measurement scale that is selected in correspondence to the desired readout precision. Additionally, however, in accordance with the example of embodiment illustrated in FIG. 3, the scale bearer displays stop notches 18 and 21 that cooperate with stop dogs 19 and 20 of the abutment 8 such that there then results, when the stop dogs 19 and 20 are introduced into the stop notches 18 and 21 by rotating the abutment 8, fixation of the abutment 8 in the uppermost position. Such an arrangement has the advantage that no loading of the actual return spring results in the case of long-term storage of the suction bottle and the vacuum prevailing therein, the return spring being loaded, rather, only when the abutment 8 is moved, by rotation, such that the stop dogs 19 and 20 are rotated out of the associated stop notches 18 and 21, so that, then, the stop dogs 19 and 20 can move downwardly in the guide grooves 22 and 23.

In the illustration in FIG. 4, the abutment 8 is illustrated such that the closure stopper 16 abuts against the support areas 17 over a thin pin 24. It is then apparent that when the outer side of the closure stopper 16 is being held fixed, the actual support area 17 can be turned by rotation (with the aid of the grip part 25) and shearing off of the pin 24. Possible by this means is detachment of the support area 17, which overlaps the closure stopper 16, from the abutment so that, then, removal of the return spring becomes possible. The leftover closure stopper 16 can then, with simultaneous squeezing of the sealing tube 7, be pressed into the opening of component 12 and therewith seals off the internal space of the sealed bottle 1, so that outflow of the wound secretion is not possible and, additionally, no connection can result between the inside of the bottle and the atmosphere, so that, guaranteed on the one hand is a positive sealing of the inside of the bottle against the outside atmosphere, but there is, on the other hand, provided the possibility that a later check of the contents of the bottle for number and type of germs is not made impossible by contact of the bottle contents with the outside atmosphere.

The scale bearer can, as is illustrated by the ring flange 26, be arranged, fixedly and/or detachably, at the top side of the suction bottle 1.

Made clear in the illustration in FIG. 5 is that non-repeatable detachment between closure stopper 16 and support area 17 of abutment 8 can also be embodied such that the support area 17a can be fixed to stopper 16 in detachable and repeatable fashion. This repeatability of detachment can be achieved through means of a threaded closure, a bayonet closure, a plug-in closure, or the like. This arrangement offers the possibility of installing or changing out the springs at the place of use so that, in this fashion, there is provided the possibility of delivering to the using hospitals bottles without a spring, the individual hospitals having a supply of springs that can be installed, so that transport costs can, in this manner, be lowered.

Furthermore, the detachability illustrated in FIG. 5 provides the advantage that doctors can install spring constants corresponding to their desires.

What is claimed is:

1. Suction bottle for sucking out secretions from wound cavities with an arrangement for checking the vacuum sealing off a pressure opening in the suction bottle, and with a connecting stub for a suction line, the improvement comprising a return spring (9) for the vacuum indicator arrangement (5), produced from a springy-elastic material, that is supported on the outside of a sealing tube (7) sealing the pressure opening (6) between the top end of the suction bottle (1) and an abutment (8) fixed to the sealing tube which is structured as an indicator arrangement and (7) which is fixed on the one end, in sealing fashion, to the suction bottle (1) and closed off on the other end, and a scale bearer for the vacuum indicator arrangement including stop notches at its top, said bearer cooperating with the abutment.

2. Suction bottle for sucking out secretions from wound cavities with an arrangement for checking the vacuum sealing off a pressure opening in the suction bottle, and with a connecting stub for a suction line, the improvement comprising a return spring (9) for the vacuum indicator arrangement (5), produced from a springy-elastic material, that is supported on the outside of a sealing tube (7) sealing the pressure opening (6) between the top end of the suction bottle (1) and an abutment (8) fixed to the sealing tube (7), which is structured as an indicator arrangement and which is fixed on the one end, in sealing fashion, to the suction bottle (1) and closed off on the other end, said abutment including two areas which are separable from each other, of which one serves as a support for the return spring and the other area serves as a fixation of the sealing tube, and including a scale bearer for the vacuum indicator arrangement, said bearer cooperating with the abutment.

3. Suction bottle in accordance with claim 2, wherein the area (16) serving for fixation of the sealing tube (7) is, at the same time, sized as the closure stopper (16) for the pressure opening (6).

4. Suction bottle in accordance with claim 2, wherein the connection between the two areas is embodied to be repeatably detachable.

* * * * *